(12) United States Patent
Wang et al.

(10) Patent No.: US 9,500,594 B2
(45) Date of Patent: Nov. 22, 2016

(54) METHOD FOR AUTOMATIC QUANTIFICATION OF DENDRITE ARM SPACING IN DENDRITIC MICROSTRUCTURES

(71) Applicant: GM Global Technology Operations LLC, Detroit, MI (US)

(72) Inventors: Qigui Wang, Rochester Hills, MI (US); James W. Knight, Davison, MI (US); Devin R. Hess, Burton, MI (US)

(73) Assignee: GM Global Technology Operations, LLC, Detroit, MI (US)

( * ) Notice: Subject to any disclaimer, the term of this patent is extended or adjusted under 35 U.S.C. 154(b) by 230 days.

(21) Appl. No.: 14/070,609

(22) Filed: Nov. 4, 2013

(65) Prior Publication Data

US 2014/0119612 A1    May 1, 2014

Related U.S. Application Data

(63) Continuation-in-part of application No. 13/757,914, filed on Feb. 4, 2013, now Pat. No. 8,942,462.

(60) Provisional application No. 61/623,145, filed on Apr. 12, 2012.

(51) Int. Cl.
  *G06K 9/00* (2006.01)
  *G01N 21/84* (2006.01)
  *G06T 7/40* (2006.01)

(52) U.S. Cl.
  CPC .............. *G01N 21/84* (2013.01); *G06T 7/401* (2013.01); *G06T 2207/10056* (2013.01); *G06T 2207/30116* (2013.01)

(58) Field of Classification Search
  None
  See application file for complete search history.

(56) References Cited

U.S. PATENT DOCUMENTS

2009/0070089 A1* 3/2009 Kawato et al. .............. 703/11
2009/0276166 A1* 11/2009 Wang et al. ................. 702/34
(Continued)

OTHER PUBLICATIONS

Caceres, C.H., et al., The Deformation and Fracture Behaviour of an Al—Si—Mg Casting Alloy, Materials Science and Engineering A197, Elsevier, 1995, pp. 171-179, Australia.
(Continued)

*Primary Examiner* — Weiwen Yang

(57) ABSTRACT

A method to automatically quantify dendrite arm spacing in dendritic microstructures. Once a location of interest in a cast material specimen has been identified, the information contained in it is automatically analyzed to quantify dendrite cell size information that is subsequently converted into a quantified dendrite arm spacing through an empirical relationship or a theoretical relationship. In one form, the relationship between DCS and DAS is such that the DAS in dendritic structure of cast aluminum alloys may be automatically determined from the measurement of one or more of dendrite cell size and the actual volume fraction of the eutectic phases in the local casting microstructure. Non-equilibrium conditions may be accounted for in situations where a theoretical volume fraction of a eutectic phase of the alloy in equilibrium condition is appropriately modified. Thus, in situations where equilibrium conditions—such as those where the casting is cooled very slowly during solidification—does not apply (such as during rapid cooling and consequent solidification), the eutectic measured in the non-equilibrium condition, which can be smaller than the theoretical value in equilibrium, can be accounted for.

13 Claims, 11 Drawing Sheets

(56) References Cited

U.S. PATENT DOCUMENTS

| | | |
|---|---|---|
| 2010/0153082 A1* | 6/2010 | Newman et al. ............... 703/11 |
| 2010/0185312 A1 | 7/2010 | Wang et al. |
| 2010/0235110 A1 | 9/2010 | Wang et al. |
| 2010/0292966 A1 | 11/2010 | Wang et al. |
| 2012/0232858 A1 | 9/2012 | Zhou et al. |

OTHER PUBLICATIONS

Radhakrishna, K., et al., Dendrite Arm Spacing in Aluminum Alloy Castings, Indian Institute of Science, AFS Transactions (80-87), 1980, pp. 695-702, India.

Spear, R.E., et al., Dendrite Cell Size, Alcoa Research Laboratories (63-55), 1963, pp. 209-215, USA.

Oswalt, K.J., et al., Dendrite Arm Spacing (DAS): A Nondestructive Test to Evaluate Tensile Properties of Premium Quality Aluminum Alloy (Al—Si—Mg) Castings, Northrop Corporation, AFS Transactions (80-51), 1980, pp. 845-862, USA.

Flemings, M.C., et al., Dendrite Arm Spacing in Aluminum Alloys, General Electric, AFS Transactions (91-176), 1991, pp. 501-506, USA.

McLellan, D.L., Modeling Microstructural Characteristics of Al—Si—Mg Castings to Develop Product Assurance, Boeing Military Airplane Co., AFS Transactions (82-78), pp. 173-191, 1982, USA.

Levy, S.A., et al., Quantitative Metallography of As-Cast Aluminum Microstructures, Reynolds Metals Co., Metallurgical Research Division, AFS Cast Metals Research Journal, pp. 93-96, Jun. 1969, USA.

Jaquet, J.C., et al., Quantitative Description of the Microstructure of Aluminium Foundry Alloys, Cast Metals, vol. 4, No. 4, pp. 200-225, 1992, Switzerland.

* cited by examiner $$DCS_{li} = \frac{L1}{7}$$

$$DAS = \frac{L2}{5}$$

METHOD FOR AUTOMATIC QUANTIFICATION OF DENDRITE ARM SPACING IN DENDRITIC MICROSTRUCTURES

STATEMENT OF RELATED CASES

This application is a Continuation-In-Part of U.S. application Ser. No. 13/757,914, filed Feb. 4, 2013, entitled Method for Automatic Quantification of Dendrite Arm Spacing in Dendritic Microstructures, which claims the benefit of U.S. Provisional Application 61/623,145, filed Apr. 12, 2012

BACKGROUND OF THE INVENTION

The present invention relates generally to the quantification of microstructural fineness of metal castings, and more particularly to the automated quantification of dendrite arm spacing (DAS) in dendritic microstructures of metal castings as a way to avoid having to take such measurements manually.

The resulting microstructure of all cast aluminum-based components (such as engine blocks, cylinder heads, transmission parts or the like) is generally determined by the alloy composition and more particularly by the solidification conditions. In hypoeutectic alloys (i.e., those that contain less of the other alloying constituents than corresponds to the eutectic composition, examples of which include but are not limited to A356 and 319), the materials tend to solidify dendritically. Other such aluminum alloy examples that exemplify dendritic solidification include 354, 355, 360, 380, 383 and others. A typical microstructure of this family of alloys consists of a primary dendritic phase and a second phase of particles such as silicon particles and iron-rich intermetallics. The relative amounts, sizes and morphology of these phases in the as-cast structure are highly dependent on the solidification condition as well as on the alloy composition. The dendrite cell size (DCS) and DAS, sometimes referred to as the secondary dendrite arm spacing (SDAS), have long been used to quantify the fineness of the casting, which in turn can be used to gain a better understanding of the material and its related properties where—as a general rule—cast components with smaller DAS tend to have better ductility and related mechanical properties. Discussions pertaining to aluminum alloy casting in general, as well as to DAS properties in particular, may be found in numerous other applications for patent that are owned by the Assignee of the present invention, including U.S. patent application Ser. No. 12/356,226 filed Jan. 20, 2009, U.S. patent application Ser. No. 12/402,538 filed Mar. 12, 2009, U.S. patent application Ser. No. 12/454,087 filed May 12, 2009 and U.S. patent application Ser. No. 12/932,858 filed Mar. 8, 2011, all of which are hereby incorporated by reference.

There have been numerous efforts at describing dendrite refinement and its relationship to the solidification condition, starting in 1950 with Alexander and Rhines, who first established a quantitative basis for the influence of composition and solidification rate on certain dendrite features. Table 1 below summarizes known literature to describe in quantitative terms the fineness of dendritic structure.

TABLE 1

Microstructural parameters describing the dendrites

| Parameters | Symbol | Unit | Definition |
| --- | --- | --- | --- |
| Dendrite arm spacing (Levy et al., 1969; Oswalt and Misra, 1980; Radhakrishna et al., 1980; Flemings et al., 1991) | DAS, $\lambda$ | μm | Distance between well defined secondary dendrite arms (center to center) |
| Dendrite cell size (Spear and Gardner, 1963; Jaquet and Hotz, 1992) | $DCS_{li}$ | μm | Randomly linear intercept among dendrite cells |
| Dendrite cell size (Cáceres et al. 1995) | $DCS_{ed}$ | μm | Area equivalent circle diameter of dendrite cells including eutectic |
| Dendrite cell count (McLellan, 1982) | CPUA | | Number of cells per field |

Of these, Spear and Gardner (1963) quantitatively described the scale of dendritic structure using DCS obtained by a random linear intercept and is referred to as $DCS_{li}$ in their FIG. 3(a). Following Spear and Gardner, Jaquet and Hotz (1992) in their study also used $DCS_{li}$ to quantify the dendrites. Levy et al. (1969), Oswalt and Misra (1980), Radhakrishna et al. (1980) and Flemings et al. (1991) all discussed DAS to quantify the dendritic structure. In these approaches, DAS is obtained by a linear intercept method where the line is chosen to intersect a series of well-defined secondary dendrite arms.

McLellan (1982) used dendrite cell count (CPUA) to quantify the microstructure and claimed that it describes the deformation process more accurately than DAS. However, Levy et al. (1969) had critically analyzed the measurements of both DAS and CPUA to characterize the cast structure, and pointed out that the standard deviation for DAS measurement was less than for CPUA measurement and also the mean cell size calculated from CPUA is greater than the mean DAS. Measurement of CPUA involves primary, secondary, and tertiary arms of the dendrites, whereas DAS measurements usually refer only to the secondary arm spacing.

The methods associated with manual measurement of DAS have been frequently used by the Assignee of the present invention as a way to make DAS measurement of aluminum castings. Such a procedure generally first includes preparation of metallographic samples that are prepared in accordance with known standards, such as the American Society of Testing and Materials Standard Guide for Preparation of Metallographic Specimens (also known as ASTM E3), a portion of which is reproduced below in Table 2.

TABLE 2

ASTM E3

| Surface | Lubricant | Abrasive Type/Size ANSI (FEPA) | Time sec. | Force[A] N(lbf) | Platen RPM[B] | Rotation |
| --- | --- | --- | --- | --- | --- | --- |
| Planar Grinding paper/stone | water | 120-320 (P120-400) grit SiC/$Al_2O_3$ | 15-45 | 20-30 (5-8) | 200-300[C] | CO[D] |
| Fine Grinding heavy nylon cloth | compatible lubricant | 6-15 μm diamond | 180-300 | 20-30 (5-8) | 100-150 | CO |

TABLE 2-continued

ASTM E3

| Surface | Lubricant | Abrasive Type/Size ANSI (FEPA) | Time sec. | Force[A] N(lbf) | Platen RPM[B] | Rotation |
|---|---|---|---|---|---|---|
| Rough Polishing low/no nap cloth | compatible lubricant | 3-6 μm diamond | 120-300 | 20-30 (5-8) | 100-150 | CO |
| Final Polishing med/high nap cloth | compatible lubricant | 1 μm diamond | 80-120 | 10-20 (3-5) | 100-150 | CO |
| synthetic suede[E] | water | 0.04 μm colloidal silica or 0.05 μm alumina | 30-60 | 10-20 (3-5) | 100-150 | CONTRA[F] |

[A]Force per 30 mm (1¼ in.) diameter mount.
[B]Power heads generally rotate between 25 and 150 rpm.
[C]High-speed stone grinders generally rotate at greater than 1000 rpm.
[D]Complimentary rotation, surface and specimen rotate in same direction.
[E]Optional step.
[F]Contra rotation, surface and specimen rotate in opposite directions.

The surface of the sample to be analyzed is expected to be of sufficient quality to reflect the truest possible size and shape of particles. In one form, the plane of the polish will include eutectic phases that will appear darker compared to the surrounding matrix. Thus, in one form, the metallographic samples are finally polished to obtain a flat, near mirror image surface finish. Chemical etching may be used to enhance the contrast of the dendrite structure, where in one form, the etching may be in accordance with ASTM E407. Preferably, the sample is clean and dry, while polishing artifacts (such as comet tailing, pitting, scratching, pullout and staining) should be kept to a minimum. Likewise, test conditions and deviations should be agreed upon beforehand. In a preferred form, each sample will be examined in numerous fields of view, each of which is subject to a high (for example, 100×) magnification, depending on the fineness of the material grain. After this, an image of the field of view to be measured should be captured. In one form, the linear intercept method may be used for measuring DAS, where three or more dendrites with visible dendrite trunks per field of view with at least three dendrite arms are selected. From this, a line is drawn from the outside edge of the first dendrite arm to the inside edge of the last dendrite arm; an example of this is depicted in FIG. 6B. The distance d for each dendrite may be recorded, while the number $n_1$, $n_2$, $n_3$, etc. of dendrite arms counted for each measurement may also be recorded. These activities may be repeated for each field of view.

At present, both a volume percentage of eutectics and the DCS can be determined automatically via the use of an image analyzer. The local cooling rate affects not only the microstructural fineness but also porosity formation. Therefore, DAS tends to be used more frequently to quantify the microstructural fineness. The problem with the measurement of DAS is that it has to be performed manually by identifying well-defined dendrite arms in the image. Unfortunately, this is both very time-consuming and heavily dependent upon the skills of the user or individual doing the measuring.

SUMMARY OF THE PRESENT INVENTION

The inability to automatically account for DAS and related material property variations of cast components is solved by the various aspects of the present invention disclosed herein, where robust, accurate and automatic measurements of DAS in dendritic microstructures of metal castings can be used for product quality control, as well as for product performance and durability analysis. In accordance with one embodiment, a method of automatically predicting a distribution of DAS and related material properties within a cast component is disclosed. The method includes taking a micro sample from the casting location of interest. In the present context, a micro sample is a metallographic sample prepared in a standard procedure for microstructural analysis. One such standard procedure includes that of ASTM E3 as discussed above. The sample is then analyzed. In one form, an image analyzer can be used for measuring DCS using either a DCS linear intercept ($DCS_{li}$) method, a mean area equivalent circle diameter method ($DCS_{ed}$) or a related approach where DCS, eutectic volume fraction and dendrite aspect ratio may be used. From this, the measured DCS value is converted to DAS according to one of the relationships presented herein. The quantified DAS value that corresponds to the DCS value is preferably put into a user-ready format, such as a printout suitable for human reading, or data in computer-readable format that can be subsequently operated upon by a computer printout device, computer-readable algorithm or other suitable means. In a preferred form, an average of the various aspect ratios measured within a particular location of interest may be used as a representation of the aspect ratio in a subsequent calculation or related algorithm.

As presently configured, the automation may take place through a program or related algorithm that can be performed, run or otherwise conducted on a digital computer in order to produce the resulting data representation of DAS. In a preferred form, the digital computer preferably includes one or more of an input, an output, a processing unit (often referred to as a central processing unit (CPU)) and memory that can temporarily or permanently store such a code, program or algorithm in the computer's memory such that the instructions contained in the code are operated upon by the processing unit based on input data such that output data generated by the code and the processing unit can be conveyed to another program or a user via output. In one form, a data-containing portion of the memory (also called working memory) is referred to as random access memory (RAM), while an instruction-containing portion of the memory (also called permanent memory is referred to as read only memory (ROM)). A data bus or related set of wires and associated circuitry forms a suitable data communication path that can interconnect the input, output, CPU and memory, as well as any peripheral equipment in such a way as to permit the system to operate as an integrated whole. Such a computer system is referred to as having a von Neumann architecture (also referred to as a general purpose or stored-program computer). Likewise, a particularlyadapted computer or computer-related data processing device that employs the salient features of a von Neumann architecture in order to perform at least some of the data acquisition, manipulation or related computational functions, is deemed to be within the scope of the present invention.

According to another embodiment, a method of automatically predicting a distribution of DAS and related material properties within a cast component is disclosed. The method includes selecting a cast material to be analyzed, using an image analyzer to automatically determine DCS information corresponding to the selected material and then converting the DCS information to DAS information through at least one of (a) an empirical relationship or (b) a theoretical relationship between DCS and DAS information.

According to another aspect of the present invention, an article of manufacture is disclosed. The article includes a computer usable medium with computer readable program code embodied therein for quantifying DAS properties of a cast material such that it can be used in a general-purpose computer or specifically-adapted computer such as discussed above. Specifically, such computer readable program code includes a portion for causing the computer to accept or read data that corresponds to digital information taken of a sample of the cast material, as well as a portion for causing the computer to process the information into DCS information, in addition to a portion for converting the DCS to DAS based on either a theoretical relationship between these two forms of information or an empirical relationship. In addition, the program that is embodied on the computer-readable medium includes a portion for outputting the DAS information. Such output may be in machine-readable or human-readable form. In this way, the determination of DAS embodied on the computer usable medium is performed in an automated way, thereby avoiding the need to acquire such information manually as discussed above. In a more particular form, the use of an image analyzer (or related equipment) to automatically determine dendrite cell size information corresponding to the cast material that has been selected may be made through using either of the $DCS_{li}$, $DCS_{ed}$ or the algorithmic combination of eutectic volume fraction and dendrite aspect ratio discussed above. Furthermore, a location to be analyzed may be determined using a standard metallographic technique (such as that corresponding to ASTM E3 mentioned above). In a particular form, the digital information that is read or otherwise accepted is in the form of digital images, such as those scannable through the image analyzer, equipment cooperative with the image analyzer or other methods known to those skilled in the art. In another particular form, the cast material may be an aluminum alloy in general and a hypoeutectic aluminum alloy in particular.

BRIEF DESCRIPTION OF THE DRAWINGS

The following detailed description of specific embodiments can be best understood when read in conjunction with the following drawings, where like structure is indicated with like reference numerals and in which.

Figure 1:
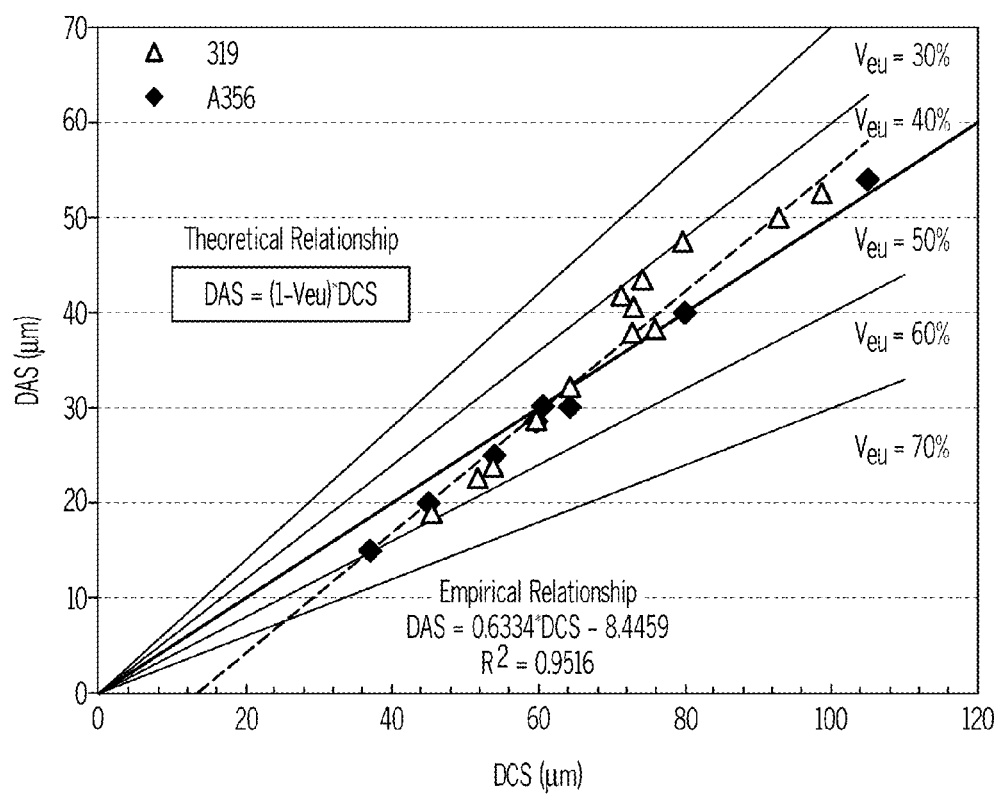
FIG. 1 is a graph depicting the disclosed DAS and DCS relationships empirically and theoretically (with varying percentages of eutectic phase volume fraction in a local microstructure) along with the measured DAS and DCS values for two different cast aluminum alloys 319 and A356.

The embodiments set forth in the drawings are illustrative in nature and are not intended to be limiting of the embodiments defined by the claims. Moreover, individual aspects of the drawings and the embodiments will be more fully apparent and understood in view of the detailed description that follows.

DETAILED DESCRIPTION OF THE PREFERRED EMBODIMENTS

Figure 7:
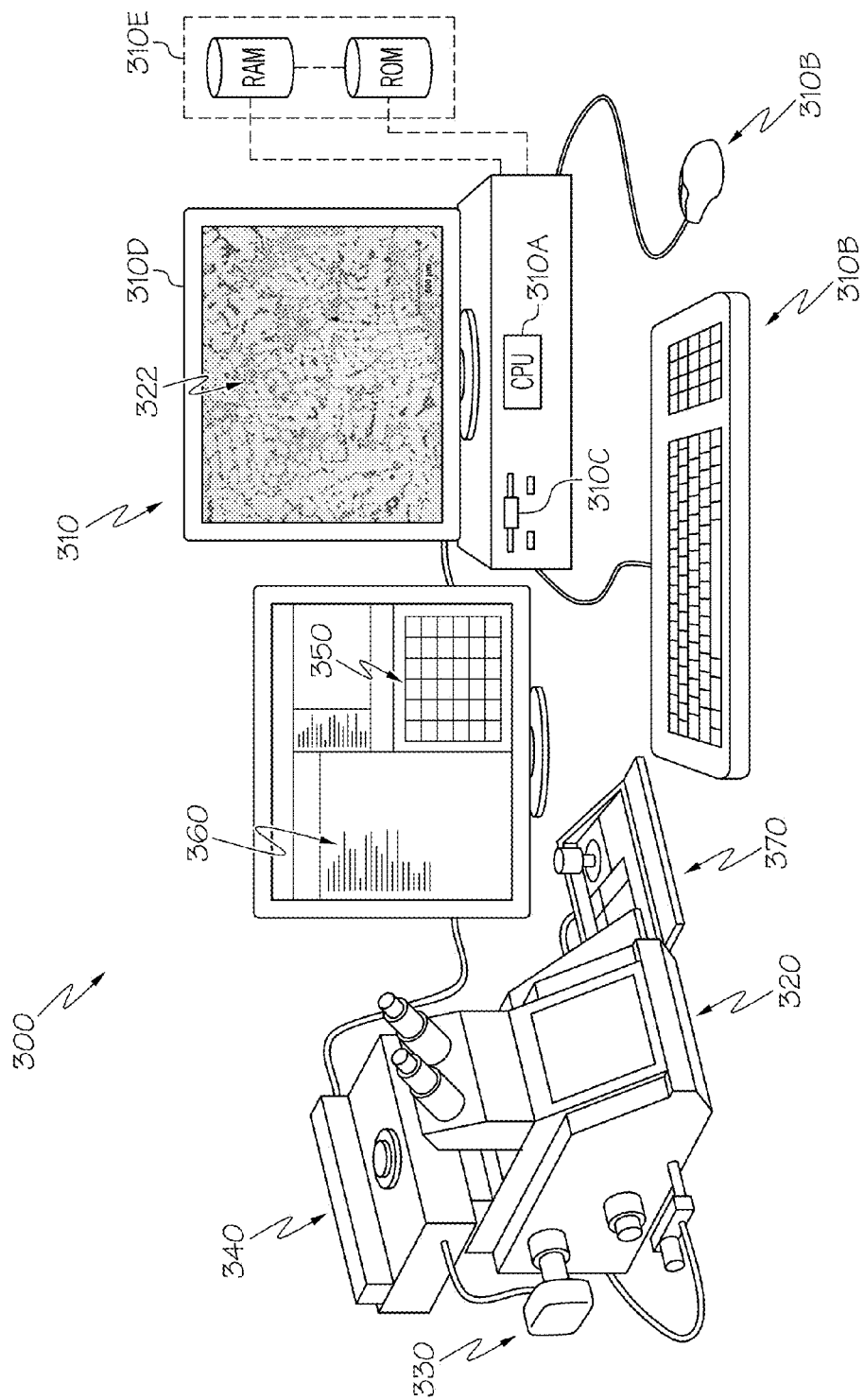
FIG. 7 shows an image analysis system that can be used to automatically quantify dendrite arm spacing according to an aspect of the present invention.

Referring first to FIGS. 1 and 7, as mentioned above, one of two approaches is used to convert a measured or sampled DCS value to DAS. As discussed above, an automated way to predict DAS distribution within a cast component may include taking a micro sample from the casting location of interest and analyzing it through a computer-based image analyzer. Referring with particularity to FIG. 7, an image analyzer system (also referred to herein as image analysis system, image analyzer or the like) 300 includes a computer 310 or related data processing equipment that includes a processing unit 310A (which may be in the form of one or more microprocessors), one or more mechanisms for information input 310B (including a keyboard, mouse or other device, such as a voice-recognition receiver (not shown)), as well as a one or more loaders 310C (which may be in the form of magnetic or optical memory or related storage in the form of CDs, DVDs, USB port or the like), one or more display screens or related information output 310D, a memory 310E and computer-readable program code means (not shown) to process at least a portion of the received information relating to the aluminum alloy. As will be appreciated by those skilled in the art, memory 310E may be in the form of random-access memory (RAM, also called mass memory, which can be used for the temporary storage of data) and instruction-storing memory in the form of read-only memory (ROM). In addition to other forms of input not shown (such as through an internet or related connection to an outside source of data), the loaders 310C may serve as a way to load data or program instructions from one computer-usable medium (such as flash drives or the aforementioned CDs, DVDs or related media) to another (such as memory 310E). As will be appreciated by those skilled in the art, computer 300 may exist as an autonomous (i.e., stand-alone) unit, or may be the part of a larger network, such as those encountered in cloud computing, where various computation, software, data access and storage services may reside in disparate physical locations. Such a dissociation of the computational resources does not detract from such a system being categorized as a computer.

In a particular form, the computer-readable program code can be loaded into ROM that is part of memory 310E. Such computer-readable program code may also be formed as part of an article of manufacture such that the instructions contained in the code are situated on a magnetically-readable or optically-readable disk or other related non-transitory, machine-readable medium, such as a flash memory device, CDs, DVDs, EEPROMs, floppy disks or other such medium capable of storing machine-executable instructions and data structures. Such a medium is capable of being accessed by computer 310 or other electronic device having processing unit 310A used for interpreting instructions from the computer-readable program code. As will be understood by those skilled in the computer art, a computer 310 that forms a part of image analysis system 300 may additionally include additional chipsets, as well as a bus and related wiring for conveying data and related information between processing unit 310A and other devices (such as the aforementioned input, output and memory devices). Upon having the program code means loaded into ROM, the computer 310 of system 300 becomes a specific-purpose machine configured to determine an optimal cast component in a manner as described herein. In another aspect, system 300 may be just the instruction code (including that of the various program modules (not shown)), while in still another aspect, system 300 may include both the instruction code and a computer-readable medium such as mentioned above.

It will also be appreciated by those skilled in the art that there are other ways to receive data and related information besides the manual input approach depicted in input 310B (especially in situations where large amounts of data are being input), and that any conventional means for providing such data in order to allow processing unit 310A to operate on it is within the scope of the present invention. As such, input 310B may also be in the form of high-throughput data line (including the internet connection mentioned above) in order to accept large amounts of code, input data or other information into memory 310E. The information output 310D is configured to convey information relating to the desired casting approach to a user (when, for example, the information output 310D is in the form of a screen as shown) or to another program or model. It will likewise be appreciated by those skilled in the art that the features associated with the input 310B and output 310D may be combined into a single functional unit such as a graphical user interface (GUI).

The image analysis system 300 is used to extract information from images 322, in particular, using metallographic techniques to relate structure to the physical properties of the material of interest. These properties would include, (but are not limited to) tensile strength, yield strength, elongation and hardness. Starting with a prepared metallographic sample, a microscope similar (but not limited) to an inverted microscope 320 is used to make an image 322 that is captured by the camera 330. Typically, many images 322 are captured through the use of a stage, often motorized, 340 and a stage pattern 350. Gray thresholding is then performed on these digitized images 322 in a computer-based routine or algorithm 360 that make up the image analysis software that may be stored in memory 310E or other suitable computer-readable medium. The routine 360 then measures the thresholded pixels of image 322. This data is then analyzed to produce the final result. A stage controller 370 (which employs joy stick-like control) is used to move the micro sample from one field to another field in the microscope 320, where the three-dimensional (Cartesean) x, y and z (focus) stage movements are controlled by the stage controller 370. This allows movement across a stage pattern to permit analyzing multiple fields of view over the sample. This automated stage pattern—which includes auto focus features—permits the capture of large amounts of data in a short period of time. The joy stick of stage controller 370 allows movement of the stage while observing the sample through the eyepiece of microscope 320 to facilitate the selection of particular areas that the analysis will be performed on.

Referring with particularity to FIG. 1, in a first approach, an empirical formula developed from the testing data for different materials is used:

$$DAS = a*DCS + b \quad (1)$$

Where a and b are material constants while in a second approach, a physics-based (i.e., theoretical) equation is used:

$$DAS = (1 - V_{eu})*DCS \quad (2)$$

where $V_{eu}$ is the actual volume fraction of eutectic phases in local microstructure. In the present context, because it is difficult and impractical to measure the actual volume fraction $V_{eu}$, a measured area fraction (which can easily be ascertained via image analyzer) is used as an equivalent. To be certain, there is a slight difference between the two, as the measured area fraction is a two dimensional representation of the eutectic phase, while the volume fraction $V_{eu}$ is a three dimensional representation. Nevertheless (where from a statistical standpoint, when all eutectic phase particles are of a spherical shape, the measured area fraction is equal to the volume fraction), the measured area fraction provides sufficient accuracy.

This second approach would provide robust and automatic measurements of DAS in dendritic microstructures of metal castings not only for product quality control but also for product performance and durability analysis. In either the empirical or physics-based (i.e., theoretical) approaches of Eqns. (1) and (2) above, the DAS in dendritic structure of cast aluminum alloys such as A356 and 319 may be automatically determined from the measurement of one or both of DCS and the eutectic volume fraction $V_{eu}$. Likewise, in Eqn. (2), $V_{eu} = k*f_{eu}$, where $f_{eu}$ is the theoretical volume fraction of eutectic phase of the alloy (in equilibrium condition), k(>1) is a coefficient to accommodate the volume fraction increase of eutectic phases with increasing solidification (cooling) rate (i.e. with reducing DAS).

The invention discussed herein is particularly well-suited for hypoeutectic metals (i.e., those with dendritic structure). Significantly, the present invention helps eliminate tedious time-consuming manual measurement of DAS, as well as reduce operator-dependent error where relatively large standard deviation (typically on the order of ±20%) may otherwise be present. This in turn provides more accurate and reliable DAS data, as well as saves the lab engineer time and cost. In one particular form, a micro sample is taken, which is then automatically analyzed in image analyzer 300 for DCS using $DCS_{li}$, $DCS_{ed}$ or the algorithmic combination of eutectic volume fraction and dendrite aspect ratio shown below in Eqn. (5). The measured DCS value is then converted to DAS according to either the empirical or physics-based (i.e., theoretical) approaches discussed above. Significantly, the method of the present invention would provide robust and automatic measurements of DAS in dendritic microstructures of metal castings that can be used not only for product quality control but also for product performance and durability analysis.

Figure 2A:
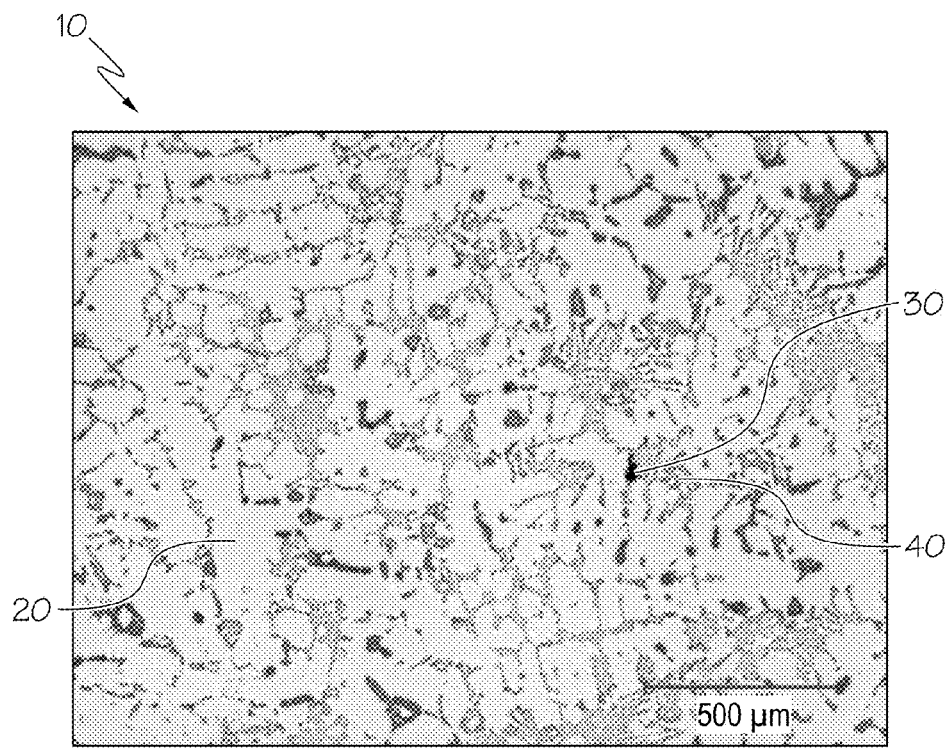
FIGS. 2A through 2E shows how an empirical and a theoretical relationship between DCS and DAS may be established through—among other things—a volume percentage of eutectic based on an image of a microstructure location of interest.
Figure 2B:
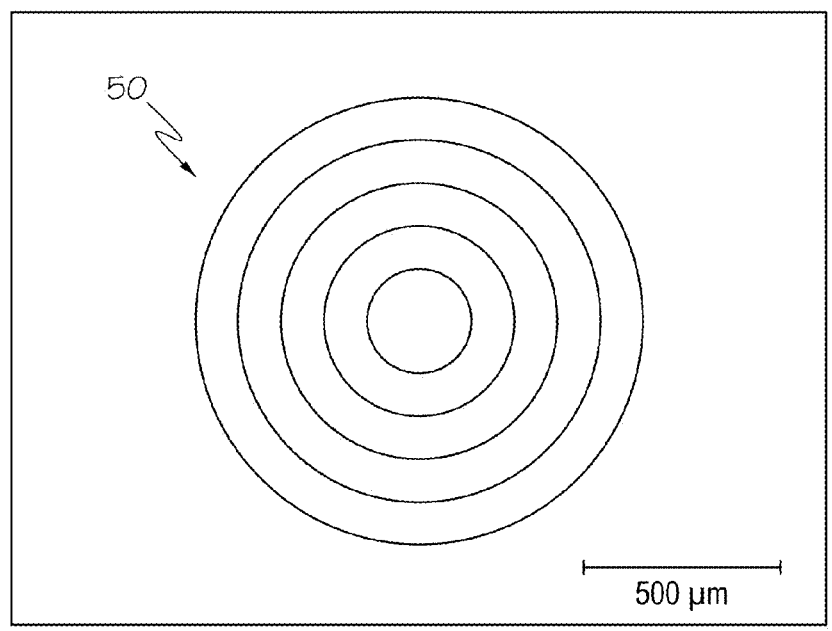
Figure 2C:
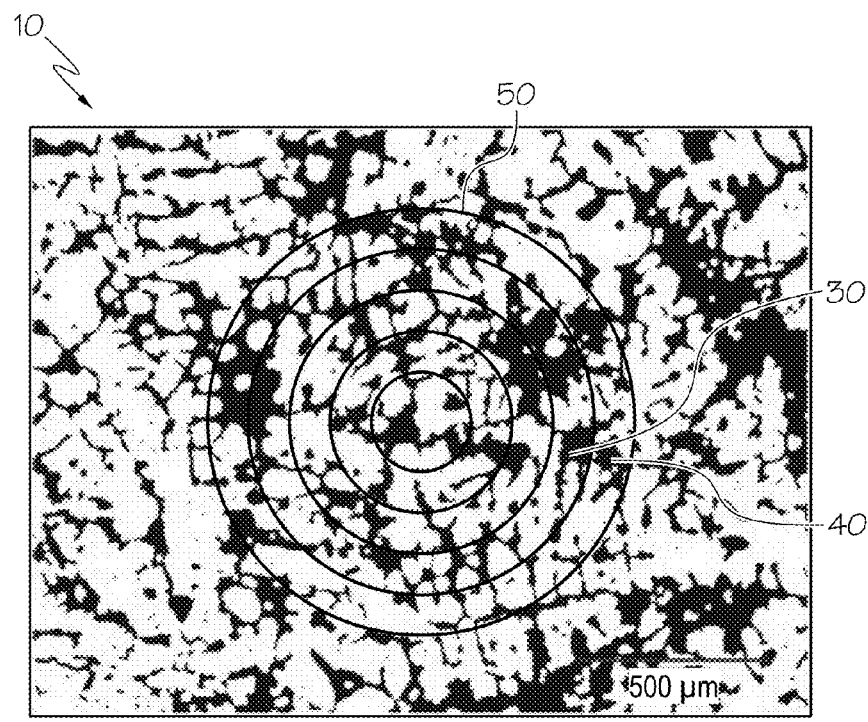
Figure 5:
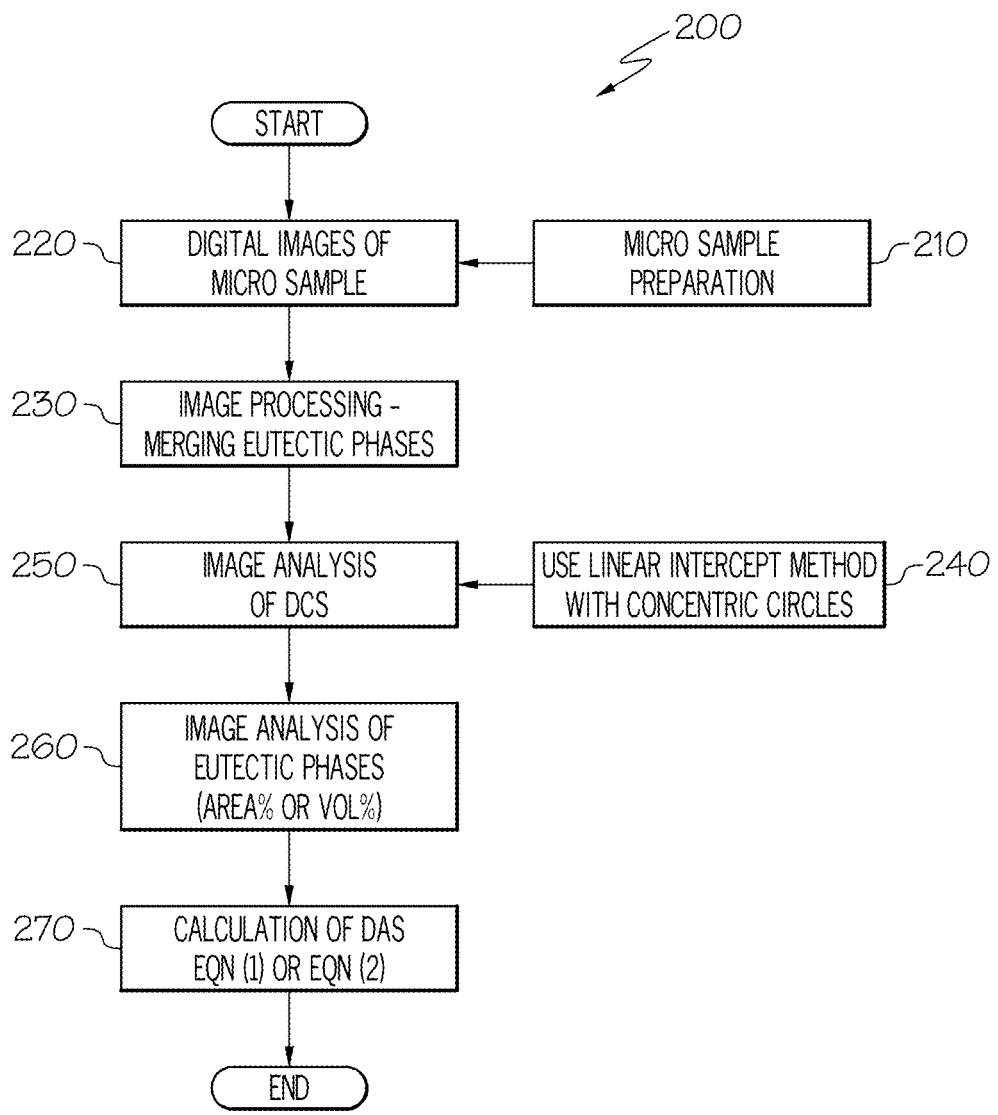
FIGS. 5 and 5A show flowcharts depicting the various steps to determining DAS according to the present invention.

Referring next to FIGS. 2A through 2D along with FIG. 5, steps associated with automatically determining DAS using $DCS_{li}$, (along with dendritic cell aspect ratios) are shown. Referring first to FIG. 2A, an image of the as-photographed microstructure 10 showing a region to be analyzed is shown. The microstructure 10 is made up of primary aluminum dendrites 20 (white) and eutectic Si and Fe-rich particles 30 (black) and eutectic aluminum 40 (which are not dendrites but instead occupy locations next to the eutectic particles 30). Referring next to FIG. 2B, five concentric circles 50 with known length (shown in exemplary form as 500 micrometers) are used as a grid (or gridded pattern) in an image analyzer system 300 (shown in FIG. 7) to estimate the DCS of the dendritic microstructure 10 shown in FIG. 2A. The value of DCS is estimated using $$DCS = \frac{L}{n} \qquad (3)$$

where L is the total length (perimeter) of the five circles and n is the total number of intercepts of the five circular lines that intercept at cell boundaries. It will be appreciated that other gridded patterns other than concentric circles may be used, so long as they provide ease of determination of DCS in the linear manner mentioned above. Referring next to FIG. 2C, the concentric circles 50 of FIG. 2B are overlaid on the microstructure 10 of FIG. 2A, while image analyzer 300 measures DCS and the volume percentage of the eutectic regions 30 and 40. FIG. 2C additionally shows the procedure of automatic measurement of DCS in an image analyzer 300, where overlapped five circle image in the processed microstructure 10 are dilated and then eroded one or more times in the image analyzer 300 to make the eutectic regions 30, 40 completely filled to determine the number of segments (interception). Thus, the processed image of the microstructure 10 as shown in FIG. 2C is then combined with the image from the concentric circles 50 in the image analyzer 300 to allow it to determine how many segments of the concentric circles 50 are broken or intercepted by the eutectic regions 30, 40. As such, the area fraction of the eutectic regions 30, 40 in an acquired location of interest of the initial image of FIG. 2A is measured through conversion of the acquired image into a eutectic image equivalent where the ratio of the darkened regions relative to the lighter regions gives a measure of the area percentage of the eutectic. It can be seen that the dark region of FIG. 2C corresponds to a merger of the eutectic particles 30 and the eutectic aluminum 40.

Figure 2D:
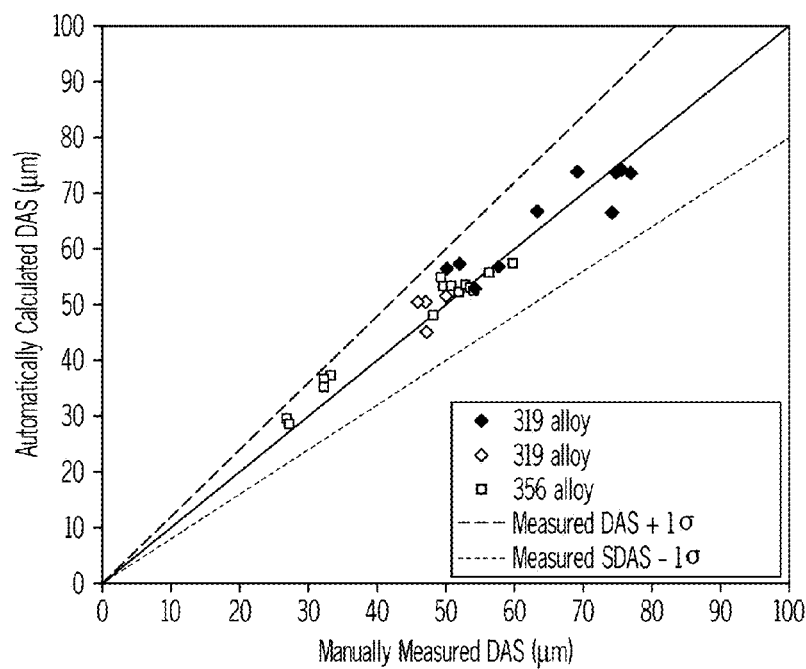

Referring next to FIG. 2D, a graph showing automatically calculated DAS using the theoretical relationship set forth in Eqn. (2) is compared against sensed or manually-measured DAS. Each data point in FIG. 2D represents both the manually measured DAS value from the horizontal axis and the calculated DAS value from the vertical axis. The solid line indicates that the calculated DAS value is exactly the same as the manually measured DAS. Two dashed lines are the average manually-measured DAS within one standard deviation of the manually-measured DAS value, and that all such data points are within this limit. Even better results have been realized though the more detailed analysis of Eqn. (5) that will be discussed in more detail below.

Figure 4:
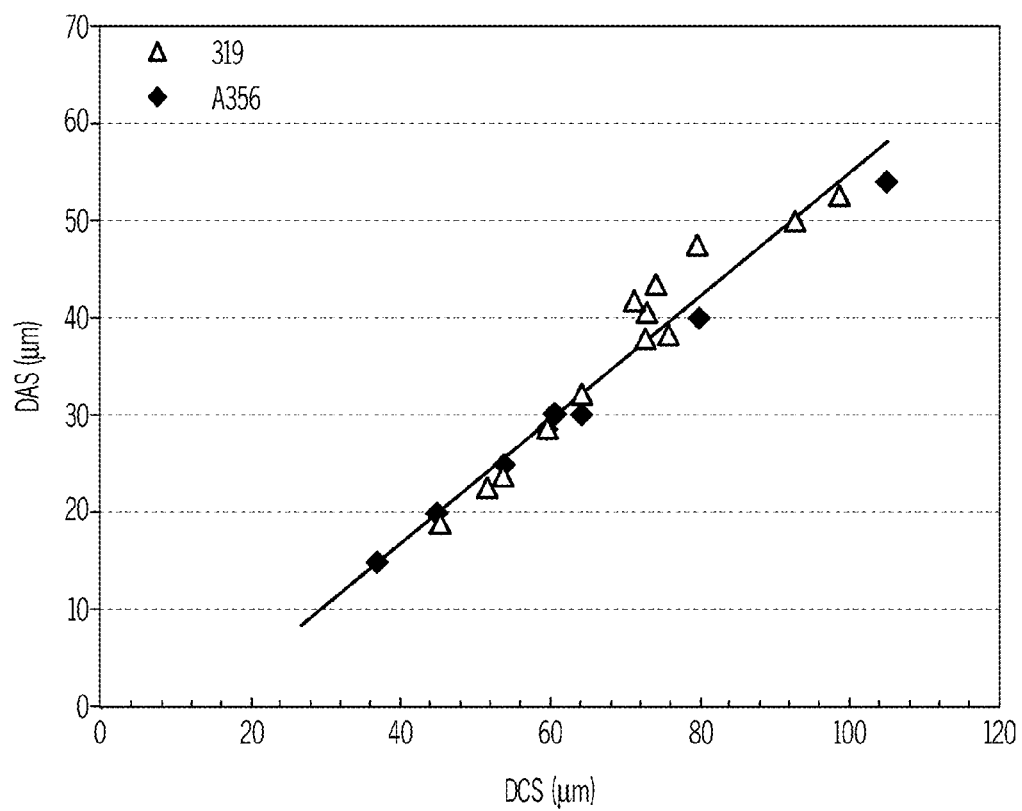
FIG. 4 shows the relationship between DAS and DCS for aluminum alloys A356 and 319 using an empirical-based relationship.

Referring next to FIG. 4, the relationship between DAS and DCS is shown, where good linear correlation between the experimental data is in evidence. Whereas FIG. 1 shows the theoretical relationship between DCS and DAS with different volumes of eutectic (noting, for example the 0,0 start), FIG. 4 (which forms a subset of FIG. 1, as the dashed line in FIG. 1 is the same as the line in FIG. 4) shows the straight line equation. After DCS is automatically determined (as mentioned above), the DAS can then be estimated empirically using Eqn. (1). For the testing data analyzed, the overall error in estimating DAS from the DCS value is within 5%, which is statistically significant. For A356 and 319 (each containing 6 to 7% Si), the empirical equation is:

$$DAS = 0.6334 \times DCS - 8.4459 (DCS > 15 \text{ μm}) \qquad (4)$$

where $R^2$ is a measure of goodness-of-fit of a linear regression; in the version depicted in FIGS. 1 and 4, $R^2$—which is a unitless fraction between 0.0 and 1.0—is 0.9516. By way of reference, an $R^2$ value of 0.0 means that knowing a value along the abscissa (i.e., x-axis) does not help in predicting the corresponding ordinate (i.e., y-axis) value. In such a circumstance, there is no linear relationship between the X and Y values, and the best-fit line is a line that can be oriented in any direction through the mean of all Y values. Contrarily, when $R^2$ equals 1.0, all points lie exactly on a straight line with no scatter such that knowledge of the X value leads to an accurate prediction of the Y value.

As mentioned above, in one form the difference between DAS and DCS is related to the volume fraction $V_{eu}$ of eutectic phases. The linear intercept method was developed by correlating measured data to a best fit straight line equation. In the linear intercept method ($DCS_{li}$) mentioned above, the DCS is equal to the value of the total length of the lines (for instance, the perimeters of five circles of concentric circles 50) divided by total number of intercepts at cell boundaries. Thus, the linear intercept method is used to get DCS values which are in turn used to convert to DAS values based on Eqns. (1) or (2) above. As such, the linear intercept method automatically acquires DAS, irrespective of whether the empirical-based approach or the physics-based approach is employed. It can be seen that the DCS value used in Eqn. (3) does not consider the width of the cell boundaries which is related to volume fraction $V_{eu}$ of eutectic phases or regions 30, 40. In other words, the DCS method overestimates the dendrite cell size by simply treating the volume fraction $V_{eu}$ of eutectic phases 30, 40 as part of dendrites 20. The volume fraction $V_{eu}$ of eutectic phases that correspond to regions 30, 40 can be significant, depending on alloy composition. In aluminum alloys A356 (7% Si) and 319 (6% Si, 3.5% Cu), the volume fraction $V_{eu}$ of eutectic phases is about 50%. It will be appreciated that the black-and-white representation of the phases or regions 30 and 40 identified in the figure makes it difficult to identify and distinguish them, as they appear to be merged together (since both are represented as black); nevertheless, it will be appreciated by those skilled in the art that other representations (such as color) could be employed to more clearly show locations of demarcation.

As mentioned above, the DAS can also be determined using physics-based Eqn. (2). For cast aluminum alloys, the theoretical volume fraction $f_{eu}$ of eutectic phases can be determined from existing phase diagrams or computational thermodynamic software known to those skilled in the art. For instance, the theoretical volume fraction $f_{eu}$ of eutectic phases is about 49% for A356 (7% Si, 0.4% Mg), and 43% for 319 (6% Si, 1% Fe, 0.5% Mn, 3.5% Cu), respectively.

In reality, the solidification of aluminum castings is never in equilibrium condition. Because of the limited solute diffusion in solidified aluminum dendrites with the increase of solidification rate, the actual volume fraction of eutectic phases $V_{eu}$ is usually greater than the theoretical value of $f_{eu}$. For alloys with high diffusivity of elements, like Si, the coefficient k varies from 1 to 1.1, while in alloys with elements having low diffusivity, like Cu, the coefficient k varies from 1 to 1.2. This is in good agreement with experimental data, as shown in FIGS. 1 and 4.

Figure 3A:
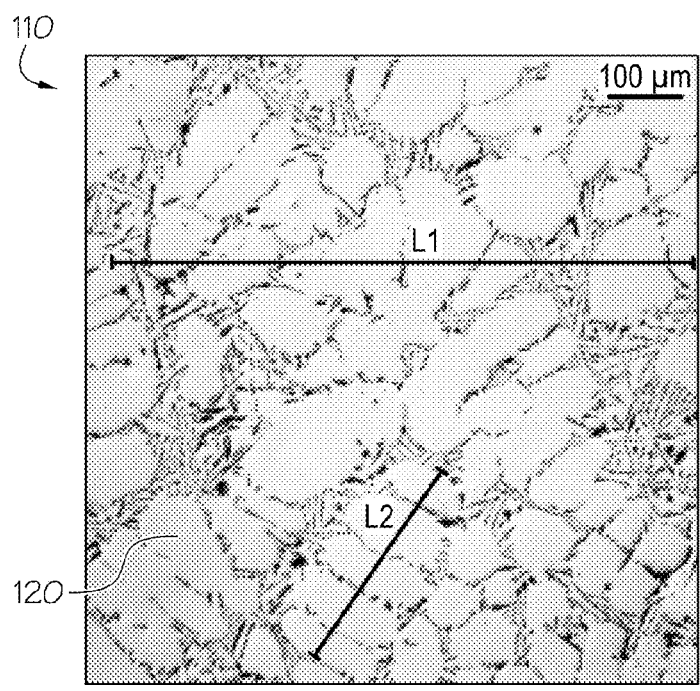
FIG. 3A shows a photomicrograph of cast aluminum alloy with the linear intercept method used to measure the size of the dendritic structure such as $DCS_{li}$, and DAS according to the prior art.
Figure 3B:
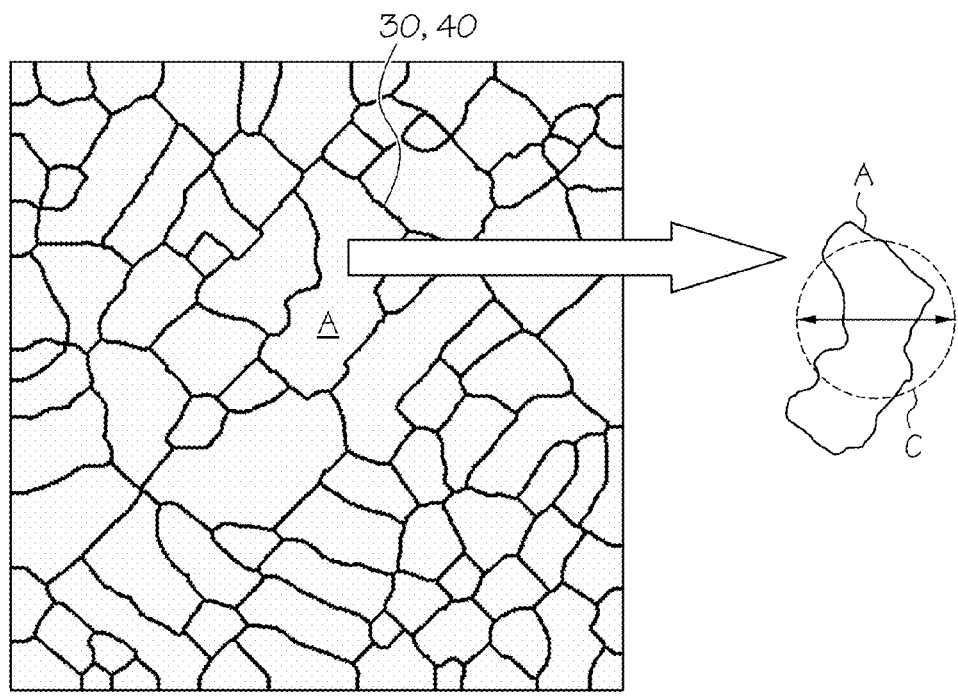
FIG. 3B shows a representation of the photomicrograph of FIG. 3A with more detail of a particular cell structure using a known semi-automatic technique where the length is divided by the number of dendrites.
Figure 3C:
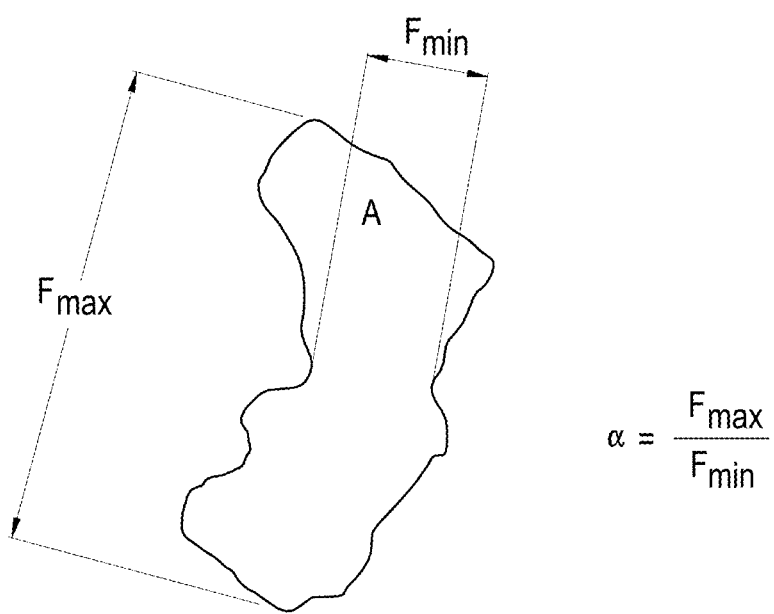
FIG. 3C shows the particular dendrite cell structure of FIG. 3B being subjected to an aspect ratio analysis.

Referring next to FIG. 3A, an example of a typical alloy microstructure 110 is shown to illustrate how the linear intercept method is used to measure the size of the dendritic structure such as DCS and DAS according to the prior art is shown. Referring next to FIGS. 3B and 3C, approaches used in the determination of DAS from acquired images such as that of FIG. 3A are shown. In particular, these figures are used in conjunction with the image analyzer 300, image analysis software and other computer-based equipment. As mentioned above, the image analyzer may be a machine (and/or software) to do advanced image editing, enhancement and analysis. In this approach, the length of L2 is divided by the number of dendrites (in this case, five) to give the DAS. In one form, the $DCS_{ed}$ parameter is defined as the average area equivalent diameter, while the Cáceres et al. reference entitled *Dendrite cell size* discussed in Table 1 above used another parameter, mean area equivalent circle diameter of dendrite cell, $DCS_{ed}$, measured by a semi-automatic technique, to define the dendrites 120. In the present context, a semi-automatic approach is one where portions of the analysis involves the use of manual steps (for example, in one or more of the middle steps). This is roughly equivalent to the measurement method of Dendrite cell size by Jaquet and Hotz that is also mentioned in Table 1. It is common to use the method shown in FIG. 3A to manually measure DAS and DCS. Referring with particularity to FIG. 3B, a result of the analysis is shown after all of the eutectic regions 30, 40 of FIGS. 2A and 2C are reduced to a line representation. As such, all of the regions (represented by area A) are considered as primary dendrite cells. The circle C has the same area as the representative region A.

Figure 2E:
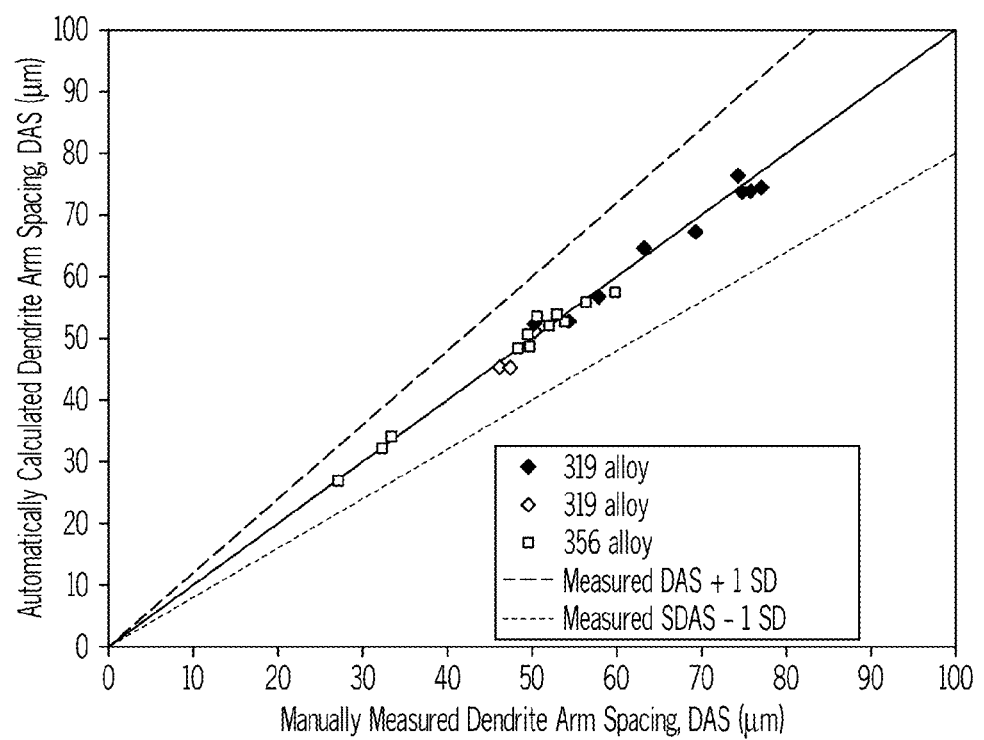

Referring with particularity to FIGS. 2E and 3C in conjunction with FIGS. 3A and 3B, the area fraction of the eutectic regions in an acquired location of interest of the image of FIG. 3A is measured by image analyzer 300 through converting the acquired image into a eutectic image equivalent where the ratio of the darkened regions (i.e., the eutectic phases or regions 30, 40) relative to the lighter regions gives a measure of the area percentage of the eutectic. This in turn can be extrapolated to give the actual volume fraction $V_{eu}$. Likewise, the aspect ratio of individual dendrite cells in the local region of interest is also measured in the image analyzer 300 after the dendrites have been processed to resemble the skeleton-like structure depicted in FIG. 3B, where the method to obtain the dendrite skeleton is adopted from Cáceres and Wang, "Dendrite Cell Size and Ductility of Al—Si—Mg Casting Alloys: Spear and Gardner Revisited", *Int. J. Cast Metals Res.*, 1996, 9, 157-162 (which is hereby incorporated by reference). From this, the aspect ratio of a particular dendrite cell A is determined by measuring the cell size along a specified direction; one way to do this is by dividing the maximum Feret (caliper) diameter $F_{max}$ with the minimum Feret diameter $F_{min}$ of the dendrite. In general, Feret diameters are especially useful in the analysis of microscopic particles, cells and related images where projections of a three-dimensional (3D) object onto a 2D plane are employed in a way such that the diameter is defined as the distance between two parallel tangential lines rather than planes. Once all of this is acquired, a relationship between the automatically measured DCS and the more desirable DAS can be formed as follows:

$$DAS = (1-V_{eu})*DCS/\sqrt{\alpha} \qquad (5)$$

where alpha ($\alpha$) is the average aspect ratio of the various cells shown in FIG. 3C. In one regard, Eqn. (5) can be seen as a more particular refinement of Eqn. (2) by taking into consideration of the square root of the average aspect ratio; such an approach produces enhanced accuracy, especially in situations where the dendrites are elongated. Such high aspect ratio situations are prevalent when DAS is of small or intermediate values.

Referring next to FIG. 5, a flowchart according to an aspect of the present invention depicts various steps 200 to automatically quantify DAS for a micro sample of a material under investigation. As discussed above, many (or all) of the steps 200 may be automated (such as through suitable algorithms configured to be operated upon by a computer or related processor-driven device). Initially, a micro sample of the material under investigation (not shown, but generally similar to that depicted in FIG. 2A) is prepared 210. In one form, the micro sample is first cut from a portion in the casting of interest. The sectioned sample is then mounted thermally with resin to form a short cylinder having the interested surface of the sectioned sample on one end of the cylinder. After mounting, the specimen is wet ground (such as with sand paper or the like) to reveal the surface of the metal. The specimen is successively ground with finer and finer abrasive media. Once the information 220 (for example, digital images) pertaining to the micro sample is made, that information may be processed 230. For example, in situations where the information is in the form of a scanned digital image, it can then be processed in a manner similar to that of FIG. 2C mentioned above. The linear intercept method (discussed above) 240 can be used to analyze the image to produce DCS information 250. From this, the DCS information is subjected to image analysis 260 based on area or volume percentages. Afterwards, DAS may be calculated 270 through one or the other of the empirically-based or theoretically-based approaches mentioned above. Such information may be output to a user or to additional post-quantification programs, routines algorithms, as well as to printout or memory devices for subsequent use.

Figure 5A:
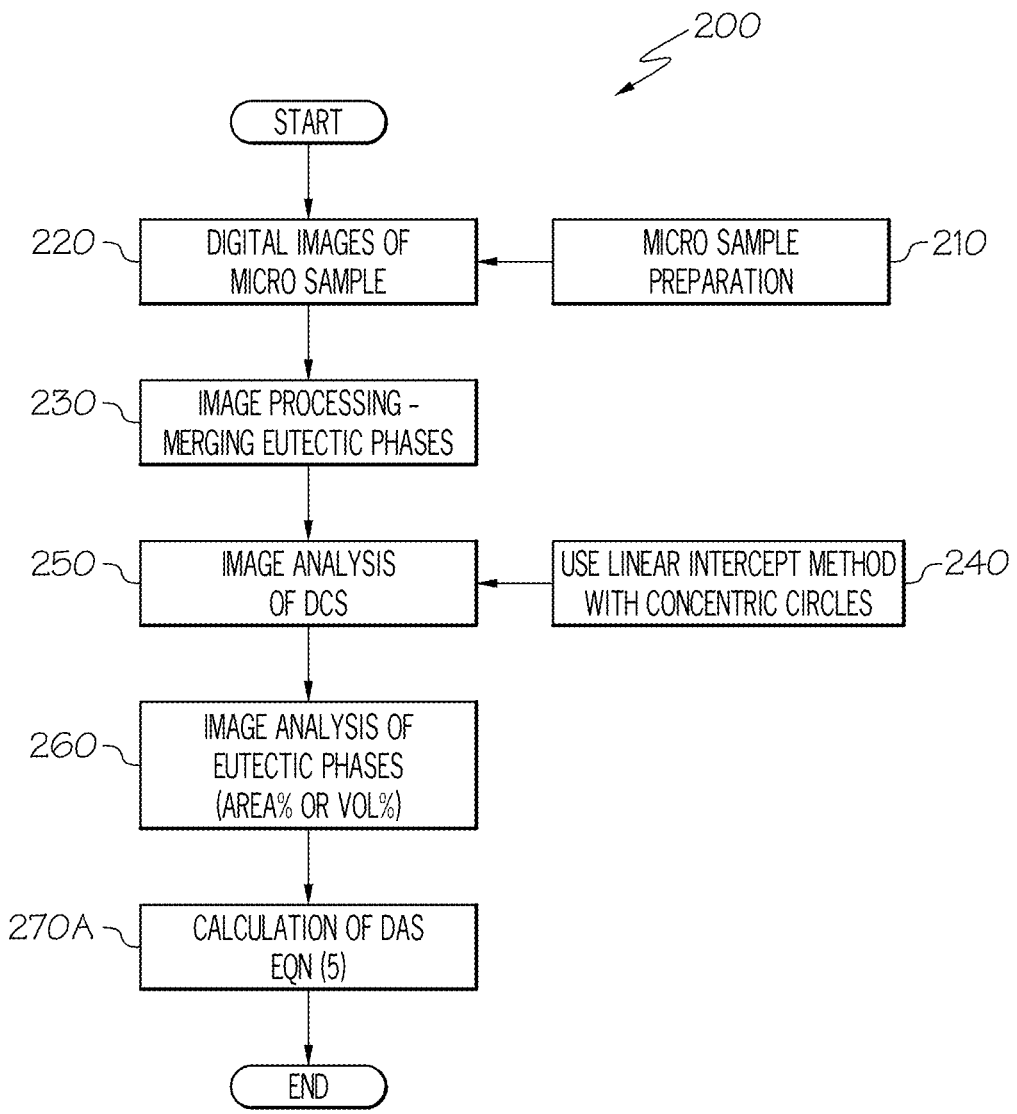
Figure 6A:
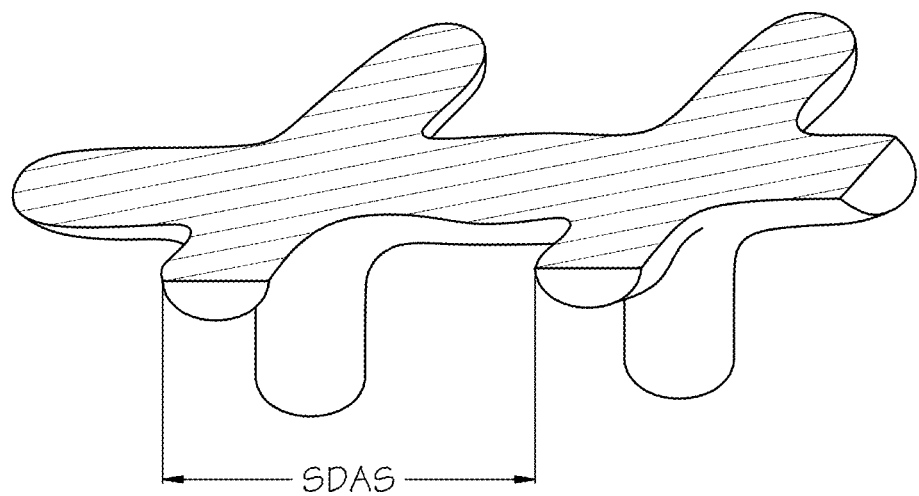
FIGS. 6A and 6B show exemplary ways to achieve DAS measurement.
Figure 6B:
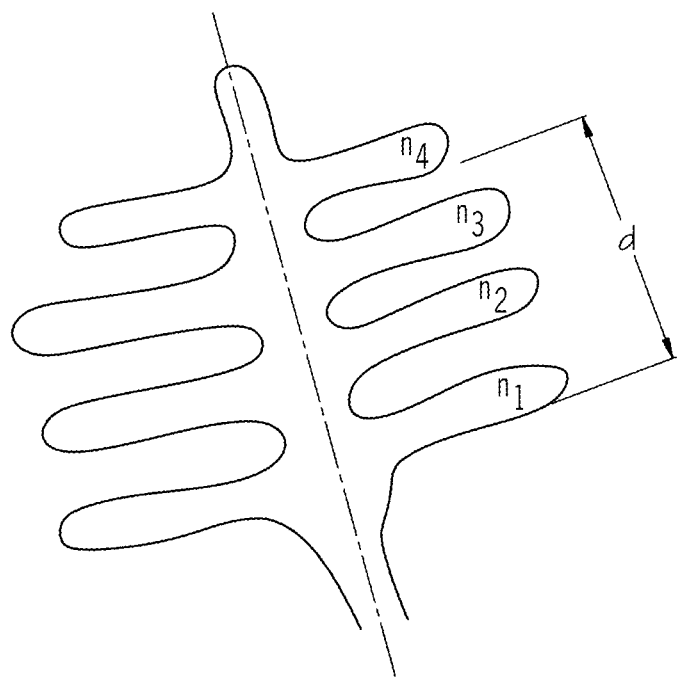

Referring next to FIG. 5A, a variation on the approach discussed in conjunction with FIG. 5 is shown, where the only difference is that the DAS calculation step 270 of FIG. 5 is replaced with the more particular calculation step 270A of Eqn. (5), taking into account the aspect ratio discussed above for the various dendrite cells within the location of interest of the image of FIG. 3A.

It is noted that recitations herein of a component of an embodiment being "configured" in a particular way or to embody a particular property, or function in a particular manner, are structural recitations as opposed to recitations of intended use. More specifically, the references herein to the manner in which a component is "configured" denotes an existing physical condition of the component and, as such, is to be taken as a definite recitation of the structural factors of the component. Likewise, for the purposes of describing and defining embodiments herein it is noted that the terms "substantially," "significantly," and "approximately" are utilized herein to represent the inherent degree of uncertainty that may be attributed to any quantitative comparison, value, measurement, or other representation, and as such may represent the degree by which a quantitative representation may vary from a stated reference without resulting in a change in the basic function of the subject matter at issue.

Having described embodiments of the present invention in detail, and by reference to specific embodiments thereof, it will be apparent that modifications and variations are possible without departing from the scope of the embodiments defined in the appended claims. More specifically, although some aspects of embodiments of the present invention are identified herein as preferred or particularly advantageous, it is contemplated that the embodiments of the present invention are not necessarily limited to these preferred aspects.

What is claimed is:

1. A method of automatically quantifying dendrite arm spacing in a hypoeutectic aluminum casting, said method comprising: using a computer-based system to acquire an image corresponding to a location of interest in said casting;
   using said computer-based system to estimate a dendrite cell size within said location of interest by overlaying said image with a gridded pattern to quantify the number of intersections between at least one cell boundary from said image and at least one portion of said gridded pattern;
   using said computer-based system to estimate a volume fraction of eutectic phases in said location of interest;
   using said computer-based system to estimate an aspect ratio of at least one dendrite cell within said location of interest; and
   using said computer-based system to convert said estimated dendrite cell size, volume fraction and aspect ratio into a quantified dendrite arm spacing and wherein said estimated dendrite cell size (DCS), volume fraction and average aspect ratio into a quantified dendrite arm spacing (DAS) is expressed by:

$$DAS=(1-Veu)*DCS/sqrt(\alpha)$$

where Veu defines said volume fraction and $\alpha$ is said aspect ratio.

2. The method of claim 1, wherein said computer-based system comprises an image analyzer to perform said acquiring and at least a portion of said determining.

3. The method of claim 1, wherein said gridded pattern comprises a series of linearly-spaced lines.

4. The method of claim 3, wherein said series of linearly-spaced lines comprises a series of concentric circles.

5. The method of claim 4, wherein said dendrite cell size is estimated by the formula $$DCS=L/n$$

where L equals a total perimeter length of said series of concentric circles and n equals the total number of intercepts between the circular lines and said at least one cell boundary.

6. The method of claim 1, wherein said aspect ratio is defined by the ratio of the maximum linear dimension of said dendrite cell to the minimum linear dimension of said dendrite cell.

7. The method of claim 1, further comprising outputting said quantified dendrite arm spacing into a user-ready format.

8. The method of claim 1, wherein said using said computer-based system to estimate a volume fraction of eutectic phases in said location of interest comprises converting said acquired image into a eutectic image equivalent.

9. A method of automatically quantifying dendrite arm spacing in a hypoeutectic aluminum casting, said method comprising:
   selecting a cast material to be analyzed;
   using a computer-based image analyzer to automatically determine dendrite cell size information corresponding to a location of interest in said selected cast material; and
   converting said dendrite cell size information to dendrite arm spacing information with said computer-based image analyzer and wherein said dendrite cell size (DCS) information to dendrite arm spacing (DAS) information is expressed by:

$$DAS=(1-Veu)*DCS/sqrt(\alpha)$$

where Veu defines said eutectic phase volume fraction and $\alpha$ defines said aspect ratio.

10. The method of claim 9, wherein said using a computer-based image analyzer to automatically determine dendrite cell size information comprises:
    acquiring an image corresponding to said location of interest; and
    estimating dendrite cell size within said location of interest by overlaying said image with a gridded pattern to quantify the number of intersections between at least one cell boundary from said image and at least one portion of said gridded pattern.

11. The method of claim 10, wherein said converting said dendrite cell size information to dendrite arm spacing information comprises:
    using said computer-based image analyzer to estimate a eutectic phase volume fraction in said location of interest;
    using said computer-based image analyzer to estimate an aspect ratio of at least one dendrite cell within said location of interest; and
    using said computer-based image analyzer to convert said estimated dendrite cell size, volume fraction and aspect ratio into a quantified dendrite arm spacing.

12. The method of claim 9, wherein said computer-based image analyzer forms part of a computer-based dendrite arm spacing quantifying system.

13. An article of manufacture comprising a non-transitory computer usable medium having computer readable program code embodied therein for automatically quantifying dendrite arm spacing (DAS) for a hypoeutectic aluminum cast material, said computer readable program code in said article of manufacture comprising:
    computer readable program code portion for causing said computer to accept data pertaining to digital information of a location of interest within a sample of said cast material;
    computer readable program code portion for causing said computer to process said digital information into dendrite cell size information (DCS);
    computer readable program code portion for causing said computer to convert said dendrite cell size information into a corresponding dendrite arm spacing through an algorithm based on a volume fraction of eutectic phases in said location of interest and an aspect ratio of at least one dendrite cell within said location of interest; and
    computer readable program code portion for causing said computer to produce an output that corresponds to said dendrite arm spacing; and
    wherein said computer readable program code portion for causing said computer to convert said dendrite cell size information into a corresponding dendrite arm spacing is expressed by:

$$DAS=(1-V_{eu})*DCS/sqrt(\alpha)$$

where $V_{eu}$ defines said volume fraction of eutectic phases in said location of interest and $\alpha$ defines said aspect ratio of at least one dendrite cell within said location of interest.

* * * * *